United States Patent [19]

Thiem et al.

[11] Patent Number: 4,859,590
[45] Date of Patent: Aug. 22, 1989

[54] ENZYMATIC SYNTHESIS OF CYCLODEXTRINS USING α-GLUCOSYL FLUORIDE AS SUBSTRATE FOR CYCLODEXTRIN α(1→4)GLUCOSYLTRANSFERASE

[75] Inventors: Joachim Thiem; Wolfgang Treder, both of Münster; Reinhold Keller, Bad Soden am Taunus; Merten Schlingmann, Königstein, all of Fed. Rep. of Germany

[73] Assignee: Hoechst Aktiengesellschaft, Frankfurt am Main, Fed. Rep. of Germany

[21] Appl. No.: 80,086

[22] Filed: Jul. 31, 1987

[30] Foreign Application Priority Data

Aug. 2, 1986 [DE] Fed. Rep. of Germany ....... 3626213

[51] Int. Cl.$^4$ ............................................. C12P 19/18
[52] U.S. Cl. ...................................... 435/97; 435/193
[58] Field of Search ................................. 435/97, 193

[56] References Cited

U.S. PATENT DOCUMENTS 3,425,910  2/1969  Armbruster et al. ............... 435/193
4,338,398  7/1982  Yoneyama ......................... 435/179

FOREIGN PATENT DOCUMENTS 61-212297  9/1986  Japan ..................... 435/97

*Primary Examiner*—Robert A. Wax
*Attorney, Agent, or Firm*—Finnegan, Henderson, Farabow, Garrett & Dunner

[57] ABSTRACT

α-Glucosyl fluoride can be converted in the presence of cyclodextrin α(1→4)glucosyltransferase into a mixture of α- and β-cyclodextrins in high yield.

6 Claims, No Drawings

ENZYMATIC SYNTHESIS OF CYCLODEXTRINS USING α-GLUCOSYL FLUORIDE AS SUBSTRATE FOR CYCLODEXTRIN α(1→4)GLUCOSYLTRANSFERASE

DESCRIPTION

Cyclodextrins are well known as products of the reaction of starch with cyclodextrin α(1→4)glucosyltransferase (E.C. 2.4.1.19) from *Bacillus macerans*. T. Ogawa and Y. Takahashi, Carbohydr. Res. 138, C5 (1985) recently succeeded with the first, complicated, chemical synthesis of α-cyclodextrin. Cyclodextrins are capable of forming inclusion complexes with a large number of physiologically active substances and therefore demand particular interest in pharmaceuticals research (M. L. Bender and M. Komiyama: "Cyclodextrin Chemistry", Springer Verlag, Berlin 1978). The following reactions which are catalyzed by cyclodextrin glucosyltransferase (CGT) are known hitherto [H. Bender, Carbohydr. Res. 78, 133 (1980); K. Wallenfels et al., Carbohydr. Res. 61, 359 (1978); H. Bender, Carbohydr. Res. 78, 147 (1980)]:

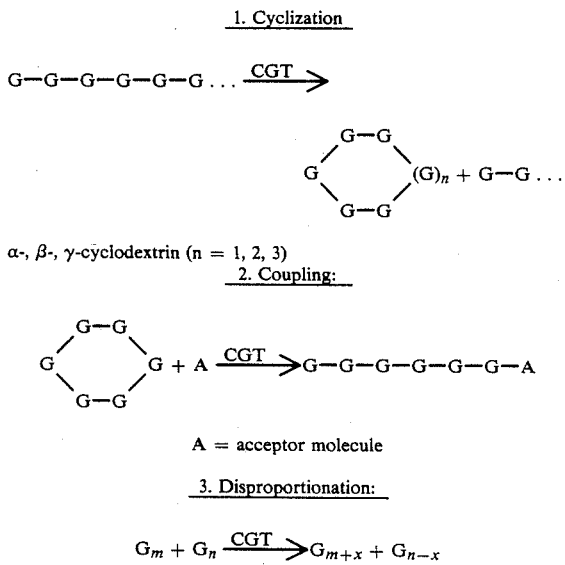

α-, β-, γ-cyclodextrin (n = 1, 2, 3)

A = acceptor molecule

In some studies, it was possible to show that certain enzymes in carbohydrate chemistry accept glucosyl fluorides as substrates for their reaction [P. J. Card and W. D. Hitz, J. Am. Chem. Soc. 106, 5348 (198); D. G. Drueck-hammer and C.-H. Wong, J. Org. Chem. 50, 5912 (1985); A. M. Gold and M. P. Osber, Biochem. Biophys. Res. Commun. 42, 469 (1971)].

Surprisingly, it has been found that the enzyme cyclodextrin glucosyltransferase {(1→4)-α-D-glucan: [(1→4)-α-D-glucopyranosyl] transferase (cyclizing), E. C. 2.4.1.19, CGT} is capable of converting α-glucopyranosyl fluoride into a mixture of cyclodextrins and maltooligomers:

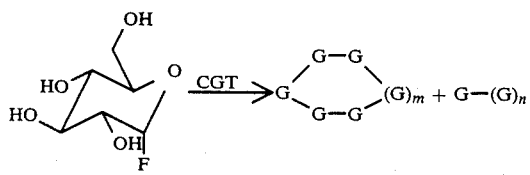

(n = 0 to 8)
(m = 1 or 2)

The invention thus relates to a process for the preparation of α- and β-cyclodextrins, wherein α-glucopyranosyl fluoride is reacted with cyclodextrin α-(1→4)glucosyltransferase.

The invention is described in detail below and defined in the patent claims.

Surprisingly, cyclodextrin α-(1→4)glucosyltransferase accepts α-glucopyranosyl fluorides as substrate. The enzyme can be employed both in free form and in immobilized form. Due to the better space/time yield, the immobilized form is preferred. For this purpose, the enzyme is generally bound adsorptively or covalently to a support, with or without a spacer. Organic supports, such as, for example, polyacrylonitrile, or inorganic supports, such as, for example, silica gel, are suitable. Covalent bonding of the enzyme to the support via a spacer, in particular glutardialdehyde, is particularly preferred.

The reaction with α-glucosyl fluoride is carried out in aqueous solution or in aqueous/organic mixtures, the ratio of aqueous solution to organic solvent being in the range 2:1 to 1:2, preferably 1:1. Suitable solvent mixtures are, for example, water/($C_1$–$C_4$)alkanols, water-/acetonitrile or water/acetone. The reaction is generally carried out at temperatures from 20° to 60° C., in particular 40 to 50° C., and a pH of 5 to 8, preferably pH 6. Due to the hydrogen halide being liberated, it is important that the pH be checked during the reaction and kept in the desired region or adjusted to a certain value either using a buffer system, for example acetate buffer, or by adding a lye, such as, for example, sodium hydroxide solution. The reaction time is dependent on the temperature selected for the reaction. In the preferred temperature range, a reaction time from 10 to 60 minutes is to be expected.

The invention is described in further detail in the examples below:

EXAMPLES

1. Immobilization of the enzyme:

Cyclodextrin α(1→4) glucosyltransferase (500 mg=~9000 units) is dissolved in 10 ml of a 0.05M sodium accetate buffer (pH 6.0) and shaken for 4 hours at 20° C. with 5 g of a glutardialdehyde-functionalized silica gel support (Grace 332 250 A) [H. H. Weetall, Meth. Enzymol. 44, 134 (1976)]. The gel is subsequently washed with 100 ml of bidistilled water, 200 ml of 1N NaCl and again with 200 ml of bidistilled water. The immobilized enzyme can now be employed directly for the reaction. The gel can be stored for more than four weeks at 4° C. without losing activity.

2. Synthesis of the cyclodextrins and maltooligomers:

1.0 g of α-glucosyl fluoride (5.5 mmol) is dissolved in 25 ml of sodium acetate buffer, pH 6.0, and the immobilized enzyme is added (1 ml of gel, ~1000 units). The reaction is carried out at 45° C. with gentle shaking, the pH being kept constant by automatic titration with 0.5M NaOH. The reaction is complete after 20 minutes, and the gel can be filtered off. For following the reaction, TLC on silica gel foils (propanol/ethanol/-water=5:3:2, v:v:v) has proven successful [K. Koizumi et al., J. Chromatogr. 321, 145 (1985)].

Yields: α-cyclodextrin: 300 mg (30%), β-cyclodextrin: 380 mg (38%); maltooligomers (glucose to maltononaose): 320 mg (32%).

$R_F$ values: α-Glc-F: 0.78; Glc: 0.68; α-cyclodextrin 0.57; β-cyclodextrin: 0.54; [γ-cyclodextrin: 0.51].

3. Analytical methods:

The reaction mixture can be separated into its components using an RP-18 HPLC column (0.8 x 50 cm, 7 μm, Merck, Darmstadt) [G. D. McGinnis et al., J. Carbohydr. Chem. 5, 83 (1986)]. At an elution rate of 3 ml/min using water as the eluent, the linear maltooligomers from the mono- to the nonasaccharide can firstly be obtained exclusively. During this time, the cyclodextrins remain on the column due to strong interactions. If, in contrast, elution is carried out with water/methanol (9:1; v:v), the linear maltooligomers are eluted as an unseparated fraction before the α- and β-cyclodextrins, which can now be separated very well.

We claim:

1. A process for the preparation of α- and β-cyclodextrins, wherein α-glucopyranosyl fluoride is reacted with cyclodextrin α-(1→4)glucosyltransferase.

2. The process as claimed in claim 1, wherein cyclodextrin α-(1→4)glucosyltransferase is employed in immobilized form.

3. The process as claimed in claim 2, wherein the cyclodextrin-alpha-(1→4)glucosyltransferase is employed bound to an inorganic support.

4. The process as claimed in claim 3, wherein the cyclodextrin-alpha-(1→4) glucosyltransferase is employed bound to silica gel.

5. The process as claimed in claim 1, wherein the reaction is carried out at temperatures from 20° to 60° C. and a pH from 5 to 8.

6. The process as claimed in claim 5 wherein the reaction is carried out at a temperature from 40° to 50° C. and a pH of 6.

* * * * *